(12) United States Patent
Akinola et al.

(10) Patent No.: US 12,057,210 B2
(45) Date of Patent: Aug. 6, 2024

(54) INTEGRATED COORDINATION OF CARE

(71) Applicant: CERNER INNOVATION, INC., Kansas City, KS (US)

(72) Inventors: Akeem Akinola, Grandview, MO (US); Lindsey McFetridge, Mission, KS (US); Jeremy Flores, Olathe, KS (US); Wes Dembinski, Lees Summit, MO (US); Grace Schreur, Overland Park, KS (US); Zach O'Bea, Mission, KS (US); John Scheeser, Blue Springs, MO (US); Sara Boswell, Blue Springs, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 307 days.

(21) Appl. No.: 16/596,356

(22) Filed: Oct. 8, 2019

(65) Prior Publication Data
US 2020/0111557 A1    Apr. 9, 2020

Related U.S. Application Data

(60) Provisional application No. 62/742,768, filed on Oct. 8, 2018.

(51) Int. Cl.
*G16H 20/60* (2018.01)
*G06F 16/23* (2019.01)
*G16H 10/60* (2018.01)
*G16H 20/30* (2018.01)

(52) U.S. Cl.
CPC ......... *G16H 20/30* (2018.01); *G06F 16/2379* (2019.01); *G16H 10/60* (2018.01)

(58) Field of Classification Search
CPC ......... G06Q 10/06; G16H 10/60; G16H 50/20
USPC ................................................ 705/2
See application file for complete search history.

(56) References Cited

U.S. PATENT DOCUMENTS

| | | | |
|---|---|---|---|
| 8,346,804 B2 * | 1/2013 | Phillips ................. | G16H 15/00 714/48 |
| 10,628,555 B1 * | 4/2020 | Bilir ...................... | G16H 10/60 |
| 2008/0059241 A1 * | 3/2008 | Zahlmann .............. | G16H 10/60 705/3 |
| 2009/0125332 A1 * | 5/2009 | Martin ................... | G16H 10/60 705/2 |
| 2012/0109686 A1 * | 5/2012 | Higbie .................. | G16H 10/60 705/3 |

(Continued)

FOREIGN PATENT DOCUMENTS

WO   WO-2014026958 A1 *   2/2014   ........... G06F 19/321

OTHER PUBLICATIONS

Google patents search, Sep. 28, 2021 (Year: 2021).*
Google patents search, Feb. 2, 2022 (Year: 2022).*
ip.com search history, Jun. 26, 2022 (Year: 2022).*

*Primary Examiner* — Dilek B Cobanoglu
(74) *Attorney, Agent, or Firm* — Invoke

(57) ABSTRACT

Systems, methods, and user interfaces provide integrated coordination of care. Care team coordination and collaboration is promoted by bringing together each of the necessary elements of a patient's plan into a single point of access. Current workflow silos that exist in the care planning space are eliminated. This allows seamless support for the many different care planning regulations across care settings and supports and involves the entire care team including the patient and personal care team.

20 Claims, 17 Drawing Sheets

(56) References Cited

U.S. PATENT DOCUMENTS

| | | | |
|---|---|---|---|
| 2013/0085798 A1* | 4/2013 | Spatola | G16H 40/20 705/7.12 |
| 2013/0304496 A1* | 11/2013 | Rangadass | G16H 50/20 705/2 |
| 2018/0301222 A1* | 10/2018 | Dew, Sr. | G16H 50/20 |

* cited by examiner

| Smith, John | DOB 02/18/1981 Weight 197 lbs | Age: 36 years MRN: 987654321 | Sex: Male FIN: 000000 | Allergies: No Known Allergies Transplant Recipient - Post-Surgery | | List | Recent | Name |
|---|---|---|---|---|---|---|---|---|

Menu - Ambulatory

| Admit | × | Discharge | × | Manage | × | Quick Orders | × | + |

Workflow
- Chief Complaint
- Plan of Care
- Vitals
- ✓ Quick Visits
- Documents
- Allergies
- Home Medications
- Diagnostics
- Histories
- Labs
- Pathology
- Microbiology
- Immunizations
- Visits
- Recommendations
- Clinical Media
- History of Present Illness
- Review of Systems
- Physical Exam
- ∗ Assessment & Plan Create Note
- ED Note (Aesthetics...)
- ED Note (Aesthetics...)
- More ▼

Plan

View: Plan ▾ [+]

Problems

| Plan Type | Status | | Action | |
|---|---|---|---|---|
| ▼ Problems | | Active Goals | | |
| 1 Hypertension | Active | 5 of 5 | This Visit | Ongoing | Resolve | Evolve |
| 2 Migraines | Active | 4 of 6 | This Visit | Ongoing | Resolve | Evolve |
| 3 Fatigue | Active | 4 of 6 | This Visit | Ongoing | Resolve | Evolve |
| ▲ Health Concerns | | | | |
| ▲ Suggested Risks | | | | |
| ▲ Wellness | | | | |

Vital Signs

[+] Latest | Last 12 months | Last 24 hours | More

| | | Jul 02, 2016 10:16 | May 21, 2016 10:00 | Mar 01, 2016 07:55 | Feb 26, 2016 13:12 | Feb 17, 2016 16:15 | Feb 02, 2016 10:16 | Jan 30, 2016 10:00 | Jan 15, 2016 07:55 | Nov 26, 2015 13:12 | Sep 17, 2015 16:15 | Feb 4, 2015 16:15 |
|---|---|---|---|---|---|---|---|---|---|---|---|---|
| BP | mmHg | 132/86 | ◆30/◆50 | -- | ◆145/◆95 | -- | 132/86 | ◆80/◆50 | -- | ◆145/◆95 | -- | -- |
| HR | bpm | -- | 100 | -- | -- | -- | -- | 100 | -- | -- | -- | -- |
| Respiratory Rate | br/min | -- | ◆25 | 17 | -- | 17 | -- | ◆25 | 17 | -- | 17 | 17 |
| Temp | degC | -- | ◆39 | -- | 37 | -- | -- | ◆39 | -- | 37 | -- | -- |
| Body Mass Index Meas. | kg/m2 | -- | -- | -- | -- | -- | -- | -- | -- | -- | -- | -- |
| Height/Length Measured | cm | -- | -- | -- | -- | -- | -- | -- | -- | -- | -- | -- |
| Weight Dosing | kg | -- | -- | -- | -- | -- | -- | -- | -- | -- | -- | -- |
| Weight Measured | kg | -- | -- | -- | -- | -- | 1 | -- | -- | -- | -- | -- |
| Pain Score | 1-10 | 1 | -- | -- | -- | -- | -- | -- | -- | -- | -- | -- |
| Oxygen Saturation | kg | -- | -- | -- | -- | -- | -- | -- | -- | -- | -- | -- |
| Head Circumference | cm | -- | -- | -- | -- | -- | -- | -- | -- | -- | -- | -- |
| Oxygen Flow Rate | | -- | -- | -- | -- | -- | -- | -- | -- | -- | -- | -- |

Upcoming Appointments

THUR | Follow-Up
Dec 30 | 9:30 a.m.
| With: Dr. Robinson

Schedule an appointment

View all Appointments (7)

Latest Results

Blood Pressure

129 / 72 mmHg — Jul 2, 2017

128 / 86 mmHg — May 21, 2017

132 / 86 mmHg (High) — Mar 1, 2017

View all Results

Allergies

Almond Oil

Steps
500 / 10,000
steps today

Blood Pressure — At Risk
129 / 72
mmHg

Calories
1,230 / 2,000
calories today

Your Suggestions

Take a Lyft Ride to your next appointment.

Promo code: FINLYFT

Powered by IBM Watson

@ John Smith

Dashboard
Your Plan
Appointments
Messaging
Health Records
Forms

@ John Smith

Your Plan 5 actions
✓ 7/12 completed

Sort by Points Available ▼

Check daily Blood Pressure
(Hypertension)                                              50

Exercise 20 minutes 3x week
(Hypertension)                                              10

You are due for your Lisinopril hydrochlorothiazide (blue pill)
(Hypertension)                                              10

Connect a Weight Tracking app
(Eating Healthy) (Hypertension)

Download local bus routes
(Transportation)                                            10

▲ Completed Focus Areas (1)

Your Plan | Your Timeline

Your Health Concerns
Hypertension
Date identified: Oct 20

Your Focus Areas
(icon) Hypertension
(icon) Eating Healthy
(icon) Transportation Your Care Team
Dr. Jones          Dr. Robinson
Care Manager       Endocrinology Your Medications
Lisinopril hydrochlorothiazide
500 mg
Take once a day with food

INTEGRATED COORDINATION OF CARE

CROSS-REFERENCE TO RELATED APPLICATIONS

This application claims priority to U.S. Provisional Patent Application No. 62/742,768, entitled "INTEGRATED COORDINATION OF CARE" and filed on Oct. 8, 2018, which application is hereby incorporated by reference as if set forth in its entirety herein.

BACKGROUND

Across health care, most care coordination is fragmented, and the care team re-invents the wheel with the care plan at each patient encounter. Caregivers in all venues, whether acute, ambulatory, post-acute or specialty, have limited coordination in the patient context. Today, the patient and their support system are not generally engaged in the decision-making or goal-setting for their own plan of care. The result is a piecemeal process where patients repeat information, clinicians start from scratch each time, and all participants have limited visibility and understanding of other care team members, as well as actions being taken towards the patient's overall plan.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces for providing integrated coordination of care. More particularly, embodiments of the present disclosure promotes care team coordination and collaboration by bringing together each of the necessary elements of the patient's plan into a single point of access. This eliminates the current workflow silos that exist in the care planning space, allows seamless support for the many different care planning regulations across care settings, and supports and involves the entire care team including the patient and personal care team.

BRIEF DESCRIPTION OF THE SEVERAL VIEWS OF THE DRAWINGS

The patent or application file contains at least one drawing executed in color. The present invention is described in detail below with reference to the attached drawing figures, wherein:

FIGS. 5-16 depict illustrative screen displays of one plan interfaces, in accordance with an embodiment of the present invention;

DETAILED DESCRIPTION

Figure 1:
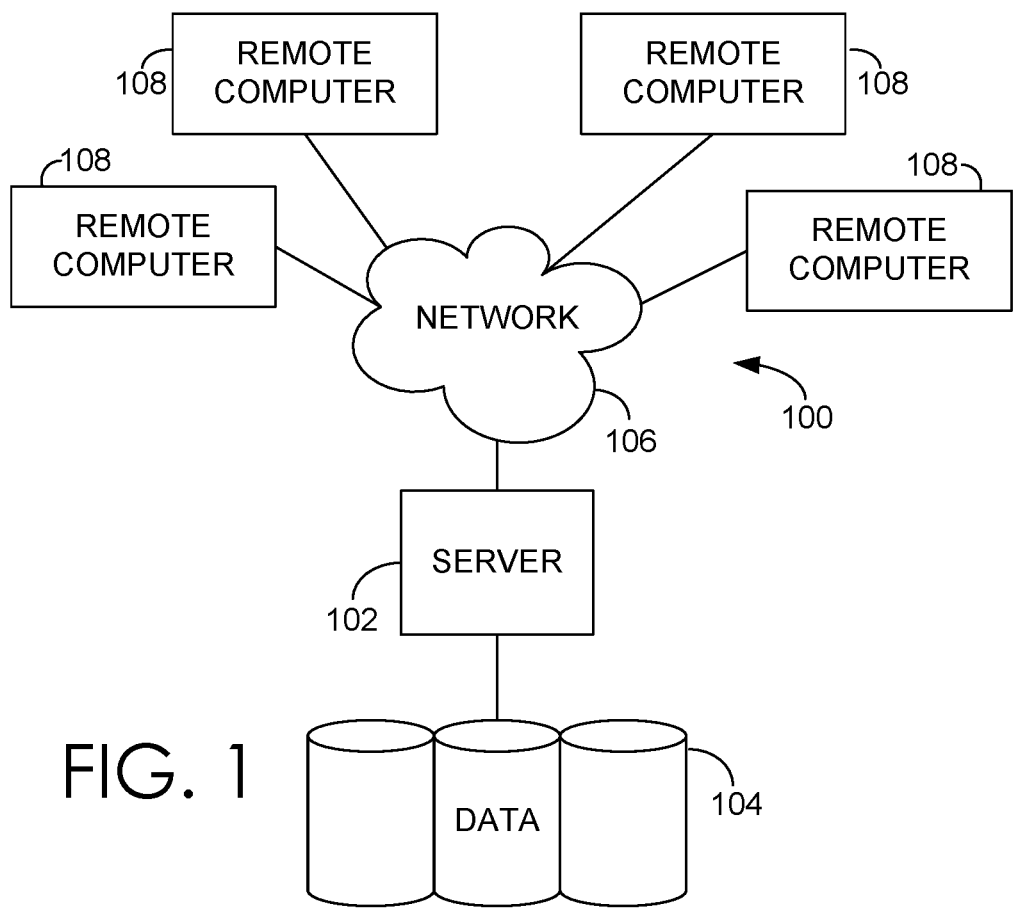
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Various terms are used throughout this description. Definitions of some terms are included below to provide a clearer understanding of the ideas disclosed herein:

A consumer, as used herein, is a person, or the single, population-agnostic representation of a person in the context of a client.

Longitudinal plan refers to an adaptive, intelligent, ambulatory-focused plan to facilitate personalized health management and care delivery to an optimal outcome. A person's longitudinal plan is not a concrete entity in and of itself and has no attributes. Rather, it is a collection of related entities such as health concerns, goals, activities, etc. As such, a person has a single longitudinal plan.

A health concern is a health focus of a person that is of concern and actively being treated or managed. A health concern may correspond to a documented condition or risk (which may be documented or derived); however, not every condition or risk will be elevated to the level of a health concern to be managed. Only those conditions or risks that are longitudinally managed by the care team (i.e., have current or historical goals, activities, etc.) will be represented by a health concern. The system allows for adding health concerns that do not correspond to documented activity, as well as non-codified health concerns (i.e., "free-text" health concerns). Examples of health concerns include conditions (e.g., diabetes, heart failure, etc., risks (e.g., fall risk), pregnancy, wellness, social determinants (e.g., access to food, lack of transportation, etc.), and the like.

A goal specifies a future target or achievement towards which the effort of care planning and execution is directed. Goals represent concrete targets to reduce or eliminate concerns or risks. A goal may exist in the absence of concerns or risks. For example, a patient may have a goal to improve his or her fitness level. Goals may or may not measurable. Measurable goals (also called targets) contain a target value to be met in order for the goal to be achieved. Non-measurable goals may still have a start and stop date, duration, etc. Additionally, goals may be short-term or long-term in nature. Goals can be used to support or make progress on addressing a defined health concern. Goals can also be associated to one or more health concerns. For example, a goal of "Stop Smoking" could help support or improve multiple health concerns. Goals can also be setup as short-term goals that support another goal. Examples of measurable goals may include: maintain HbA1c<7.5%, lose 10 pounds in four weeks, walk ten thousand steps per day, obtain relief from back pain, and the like. Examples of non-measure goals may include: increase strength and endurance, walk with a steady gait, remain free from drinking alcohol, and the like.

An activity refers to an action that is carried out to support or reinforce the patient's health and wellness. Activities can support and be associated with one or more health concerns. Activities can also support and be associated with one or more goals. Examples of activities may include: medication (e.g., take 500 mg Metformin two times daily), monitoring (e.g., use blood pressure device daily), assessment (e.g., take the Asthma Control Test (ACT)), education (e.g., enroll in diabetes education course), instruction (e.g., use a shower bench when bathing), physical (e.g., exercise three times a week), and the like.

Strengths, as used herein, is defined by the Adult Needs and Strengths Assessment (ANSA), which defines a strength as "individuals assets; areas of life where she is doing well or has an interest or ability." In order to follow a strengths-based care planning process, the longitudinal plan supports documenting what the strengths of a person are and describes how the care plan is centered on those strengths.

A care team is the set of people who are actively managing and/or making decisions about a person's health. Some care team members may be represented as personnel or consumers, and can interact with the longitudinal plan directly through solutions, whereas other members (such as power of attorney, some family members) may not. Examples of care team members include: primary care provider, care manager or care coordinator, specialist, person or consumer (i.e., the subject of the plan), power of attorney, legal proxy, family member, and the like.

As noted in the Background, most care coordination is fragmented and the care team re-invents the wheel with the care plan at each patient encounter. Caregivers in all venues, whether acute, ambulatory, post-acute or specialty, have limited coordination in the patient context. Today, the patient and their support system are not generally engaged in the decision-making or goal-setting for their own plan of care. The result is a piecemeal process where patients repeat information, clinicians start from scratch each time, and all participants have limited visibility and understanding of other care team members, as well as actions being taken towards the patient's overall plan.

Currently, the many parts of the plan of care (goals, interventions, outcomes, orders, activities, barriers, problems) reside in various sections of the chart creating a siloed workflow and view of the patient's plan of care, does not allow the care team to manage ongoing conditions across visits and makes it much more difficult for the care team to coordinate care for the patient. Additionally, the entire plan cannot be pulled together, printed, electronically signed, sent to the portal or support patient and personal care team interaction or updates.

Embodiments of the present disclosure provides integrated coordination of care around longitudinal health concerns directly into a workflow of a care team member. The integrated coordination of care utilizes existing components (such as personnel ministry, consumer ministry, longitudinal record, etc.) while introducing several new components and services, such as longitudinal activities, goals, and health concerns and strengths. Functionality is exposed primarily through public APIs and an embeddable SMART application.

Embodiments of the present disclosure promotes care team coordination and collaboration by bringing together each of the necessary elements of the patient's plan into a single point of access. This eliminates the current workflow silos that exist in the care planning space, allows seamless support for the many different care planning regulations across care settings, and supports and involves the entire care team including the patient and personal care team.

Plans of care are started with every admission, reviewed at every visit and utilized to report to physicians/insurance companies/vested parties regarding a patient's progress, and are highly scrutinized by regulatory bodies and surveyors.

Plans of care are a critical piece of the workflow in all venues of care. Additionally, as health care transitions to a value-based payment system, care coordination including the client's and patient's ability to manage the care plan will be critical to succeed in these new models with impacts to outcomes, costs, resources, services utilization, etc.

Embodiments of the present invention provide a collaborative, problem-solving approach to these current state challenges and in meeting the changing market and industry demands driving towards a comprehensive care plan, including how we support our clients through changing reimbursement models, regulatory demands, as well as driving improved patient outcomes and putting patients in the driver's seat of their own plan of care.

Embodiments of the present invention pull together into a one-stop-shop and holistic view all of the plan of care elements, allowing the plan to fully support care team coordination and communication, reducing time spent in double documentation to update the plan of care separately and result in a cleaner view of the patient's plan of care, progress towards goals and support the care team in driving improved outcomes for the patient. Embodiments of the present invention also support clients in meeting regulatory requirements related to goals, health concerns, and patient-centered interaction with the plan.

Accordingly, one embodiment of the present disclosure is directed to one or more computer storage media having computer-executable instructions embodied thereon that, when executed by a computer, causes the computer to perform operations. The operations include enabling a clinician to select a plan template from a plurality of plan templates. The operations also include attaching the plan template to a patient identifier corresponding to the patient. The operations further include integrating the plan template with a wellness plan of the patient. The operations also include enabling the patient to update the wellness plan via a portal.

In another embodiment, the present disclosure directed to a computerized method. The method comprises enabling a clinician to select a plan template from a plurality of plan templates. The method also comprises attaching the plan template to a patient identifier corresponding to the patient. The method further comprises integrating the plan template with a wellness plan of the patient. The method also comprises enabling the patient to update the wellness plan via a portal.

In yet another embodiment, the present disclosure is directed to a system. The system comprises: a processor; and a computer storage medium storing computer-usable instructions that, when used by the processor, cause the processor to: enable a clinician to select a plan template from a plurality of plan templates; attach the plan template to a patient identifier corresponding to the patient; integrate the plan template with a wellness plan of the patient; and enable the patient to update the wellness plan via a portal.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home health care environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire health care community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote health care device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
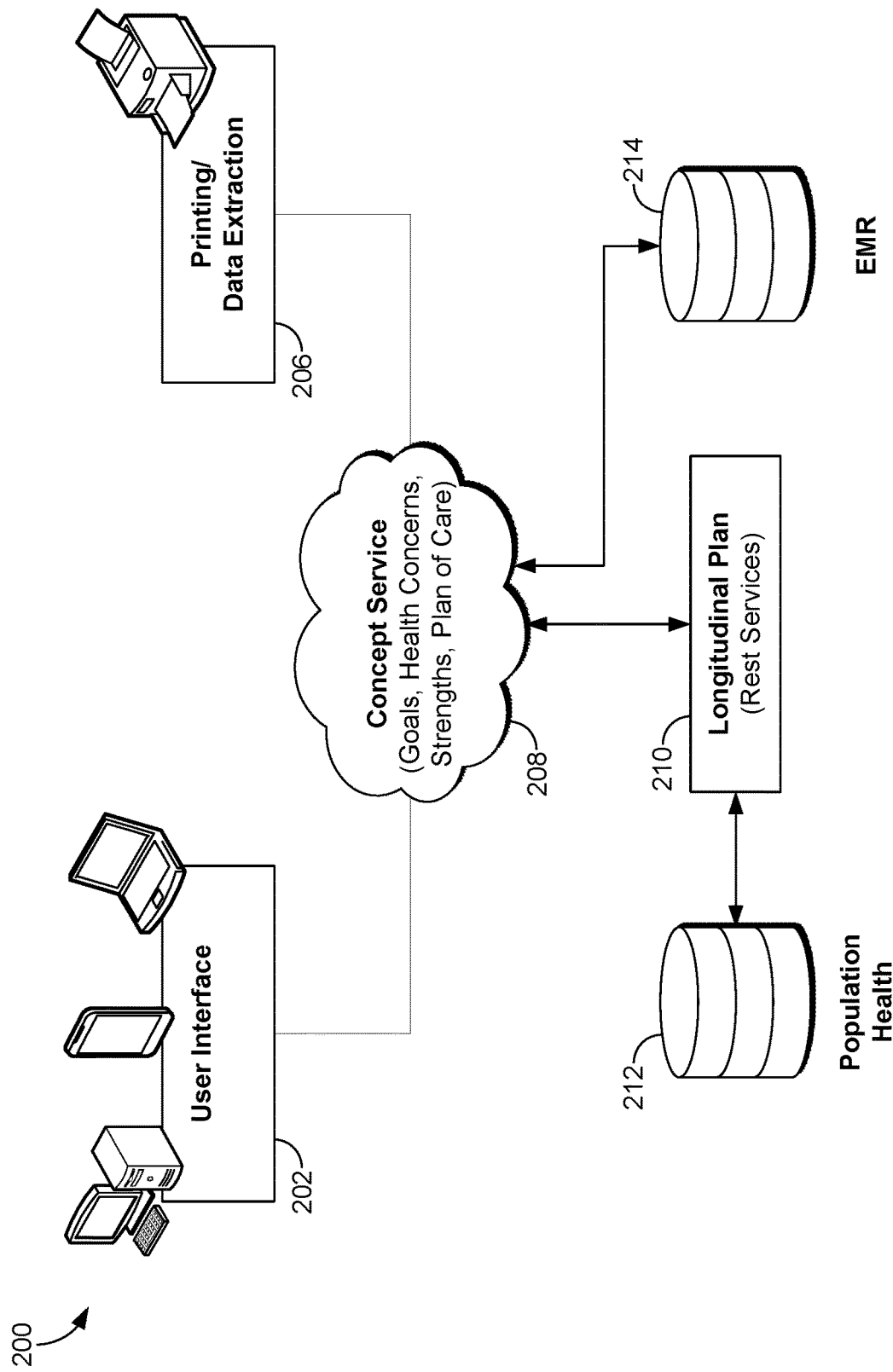
FIG. 2-4 depicts an exemplary framework of a one plan system suitable to implement embodiments of the present invention.

Turning now to FIG. 2, an exemplary framework of a one plan system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The one plan system 200 may be implemented via any type of computing device, such as computing device 100 described above with reference to FIG. 1, for example.

In the one plan system 200, outpatient and inpatient/acute data 214 are stored as different models but served up as the same concept using the same visual component, regardless of where these currently reside, while still supporting all the different solutions, form factors, platform-specific codifications, venues and disciplines interacting with the plan. In one embodiment, a concept service 208 (i.e., REST ALVA services) is utilized alongside various healthcare platforms (e.g., CERNER's ORION/TERRA platforms) to manage and retrieve all concepts for the patient's plan 210. As can be appreciated, this provides a consistent and streamlined approach to care planning.

In previous models there were several ways to access raw data which provided flexibility to consumers on how to retrieve data. However, this led to incorrect assumptions and challenges between consumers on how to represent data. The one plan system 200 streamlines this by aggregating and serving up data through the concept service 208. With population health data 212 as an additional layer under the concept service 208, managing and keeping the data synchronized becomes challenging, and consumers may incorrectly assume or handle the logic. The one plan is able to aggregate all dependencies into their respective relevant concepts thereby exposing the right data/structure needed for all consumers, whether accessing via a user interface 202 or printing/data extraction services 206.

Figure 3:
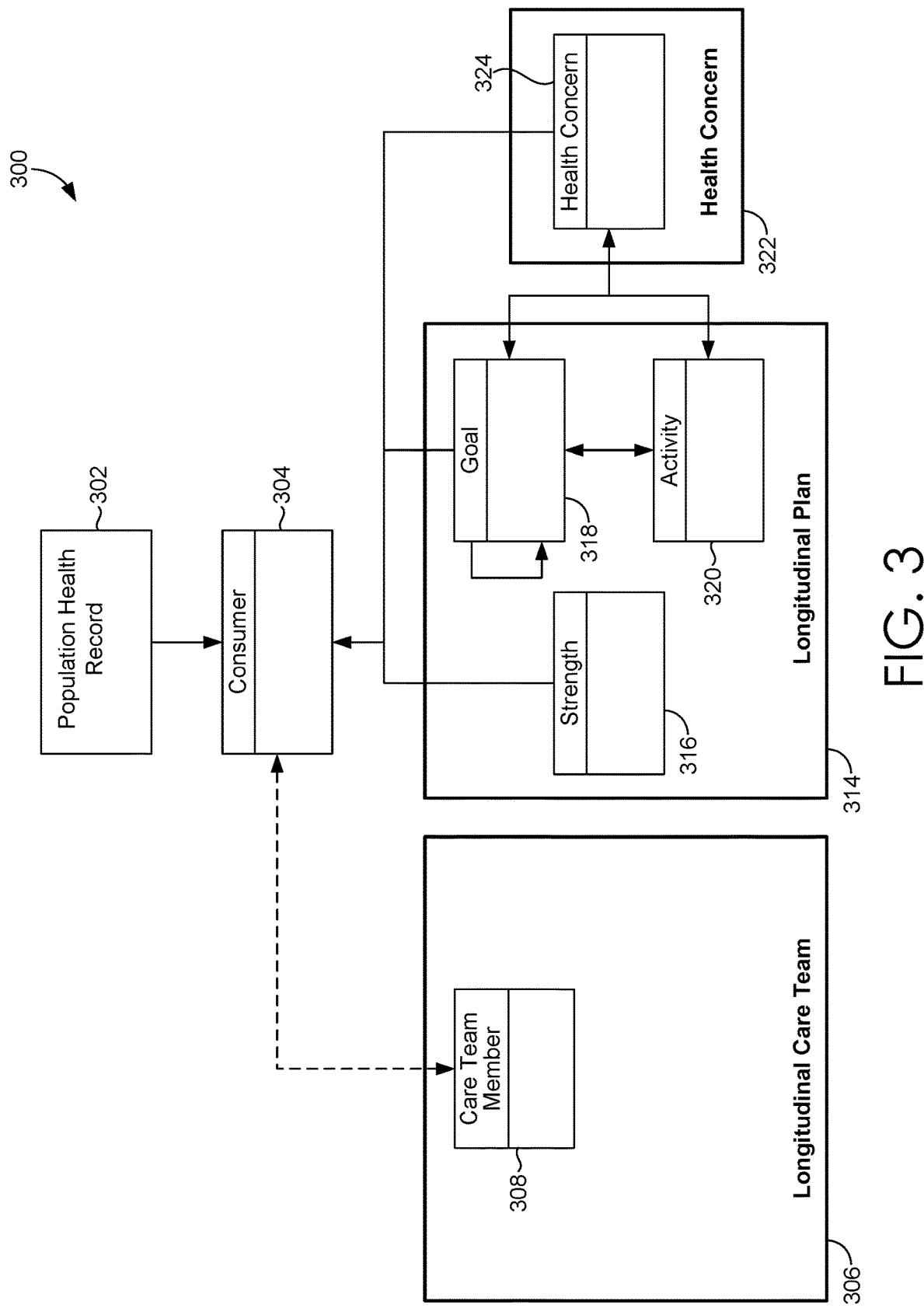

In FIG. 3, an exemplary framework of a one plan system 300 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The one plan system 300 may be implemented via any type of computing device, such as computing device 100 described above with reference to FIG. 1, for example.

As shown in FIG. 3, a one plan system 300 is depicted showing the relationship between a care team 306 managing an individual's care delivery, a longitudinal plan 314, and the individual's health concerns 322. As illustrated, the care team 306 comprises a care team member 308. The care team member 308 may include a primary care provider, a care manager or care coordinator, a specialist, a power of attorney, a legal proxy, or a family member. Each of the components of the one plan system 300 may be accessible by a consumer 304 (i.e., the subject of the plan) via a consumer application. Additionally, a population health record 302 may be exposed to the consumer via the consumer application.

The longitudinal plan API 314, as described in more detail below, comprises a strength component 316, a goal component 318, and an activity component 320. The longitudinal plan API 314 facilitates creating the individual elements of the longitudinal plan (goals, activities, strengths, etc.), creating relationships between the individual elements, and utilizing reference content that can be used to help users create meaningful codified plan elements. The relationship between plan elements and external resources can also be managed (e.g., health concerns).

The health concern API 322, as described in more detail below, generally enables adding and managing health concerns 324 for consumers. The health concern API 322 also enables curating, searching, and retrieving health concern reference content.

Figure 4:
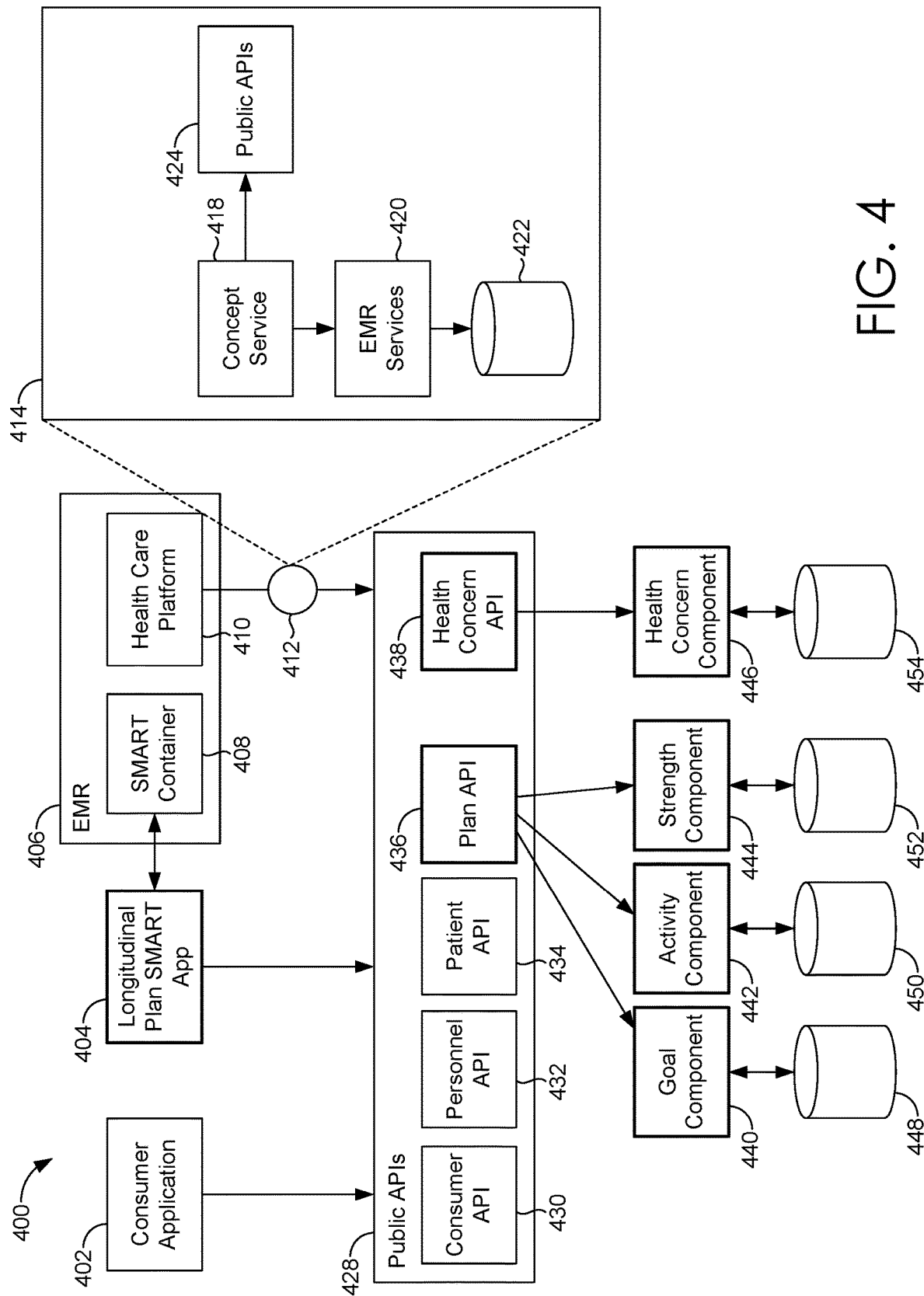

Referring now to FIG. 4, an exemplary framework of a one plan system 400 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The one plan system 400 may be implemented via any type of computing device, such as computing device 100 described above with reference to FIG. 1, for example. The one plan system 400 includes, among other components, a consumer application 402, a longitudinal plan SMART application 404, an electronic medical record (EMR) 406, a population health component 414, and a public API component 428.

The public API component 428 generally provides a publicly accessible endpoint for managing all aspects of the care plan for a consumer. This includes creating the individual elements of the longitudinal plan (goals, activities, strengths, etc.), creating relationships between the individual elements, and utilizing reference content that can be used to help users create meaningful codified plan elements. The relationship between plan elements and external resources can also be managed (e.g., health concerns).

As shown, the public API component 428 comprises a consumer API 430, a personnel API, 432, a patient API 434, a longitudinal plan API 436, and a health concern API 438. Each of the various APIs provided by the public API component 428 enables various components of the one plan system 400 to access the care plan for the consumer.

As illustrated, the longitudinal plan API 436 comprises three components: goal component 440, activity component 442, and strength component 444. Goal component 440 generally enables adding and managing goals for consumers and curating, searching, and retrieving goal reference content. Activity component 442 generally enables adding and managing activities for consumers and curating, searching, and retrieving activity reference content. Strength component 444 generally enables adding and managing strengths for consumers and curating, searching, and retrieving strength reference content.

Health concern API 438 generally enables consumers and members of their care plan to create and manage health concerns. For example, a consumer can manage health concerns via a consumer application 402. Health concerns are a meaningful aspect of managing overall health and wellness. Because health concerns are generally useful outside of the context of care planning, health concerns are maintained in a separate set of public APIs. A set of reference content can also be maintained to allow for the creation of codified health concerns from a prebuilt set of templates.

In addition to public APIs for EMR integration into native workflows, a SMART-enabled application, longitudinal plan SMART application 404, allows for standalone workflows to be embedded in EMRs 406 that support the SMART standard 408. Additionally, the longitudinal plan SMART application 404 consumes the same public APIs 428 that are used for EMR integration, rather than calling internal microservices directly.

EMR integration is achieved via a "services integration" pattern. Population health public APIs 424 are consumed by concept services 418, which in turn is called by healthcare platform 410. Concept services 418 utilize a population health consumer lookup API 420 to translate EMR person identifiers to population health consumer identifiers. The population health consumer identifiers may be stored in database 422. Existing dependent services that store document-oriented data generated by map-reduce processing (such as personnel, longitudinal record, etc.) may also be stored in database 422.

Services that require storage of relational data (e.g., goal component 440, activity component 442, strength component 444, health concern component 446) may utilize a database cluster 448, 450, 452, 454 for high availability and fault tolerance.

In practice, the longitudinal plan is a cloud-based, cross-discipline, cross-venue care plan and is not confined to a single EMR or system. This is advantageous in that it allows users across different systems (such as different EMRs, patient portals, etc.) to view and interact with the plan, however, there are situations where some information may need to be saved in a local EMR and also represented in the longitudinal plan. In these situations, manual double documentation can be reduced and information between both systems can be correlated with one another or created based on each other.

The longitudinal plan supports a concept of a health concern, which is a health-related issue about a person that is of concern to someone. The concept of a health concern has a clear overlap with the concept of problems in an EMR. To seamlessly create a health concern based on an already-documented problem in an EMR, and vice-versa, and quickly correlate and compare the two lists is facilitated because health concerns are primarily represented by a code roll-up in an ontology. By representing a health concern as a code roll-up (a "concept"), if an item in an EMR is represented by a code (such as a problem), that code can be used and compared to the codes in the concept for a health concern. If the code is contained in the concept, that information can be used to either seamlessly create a new health concern for a person if it does not already exist, or return information back about the person's current health concern that correlates to the problem. By doing so, the EMR has flexibility around how it wants to represent a health concern in the context of a person's documented problems, and it can build workflows around creating a health concern based on problems that are documented, that do not require a person to manually double-document.

The focus of the longitudinal plan is on the goals and activities that cross healthcare encounters and it represents the expectations and instructions for a person that are not limited to a given episode of care. This makes the longitudinal plan an ideal place for care plan items that would be generated in an ambulatory or outpatient setting. However, there are care planning workflows that still occur within an inpatient setting, where the care plan is primarily focused on what needs to happen within that episode of care. These types of care plans are referred to as "episodic" care plans, in order to differentiate them from the longitudinal plan. Since these episodic plans are specific to an episode, they also require deep integration with the EMR used in that episode, to drive things like tasks, documentation, and result evaluation.

Even though there is a difference between episodic and longitudinal care plans, one can influence the other. For example, a person who has an inpatient stay for a knee replacement will likely have an episodic care plan documented by their nurses that will contain various goals and activities focused on the person's recovery in the hospital. There could be new goals and activities established in the episodic care plan (goals around mobility, for instance, or activities for certain stretches or exercises the person should do) that may begin in the episodic care plan, but the clinicians may want the person to continue tracking them after discharge. To facilitate this, items in an EMR's episodic care plan are correlated to items in the longitudinal plan. This is another area where concepts, or code roll-ups, can facilitate situations where it can be determined if a codified item in an EMR is conceptually similar to an item in the longitudinal plan. Similar to what was outlined for health concerns, a codified episodic goal or activity could match the concept on a longitudinal goal or activity, and in doing so, the EMR may determine if there are any existing items on the person's longitudinal plan that match what the clinician wants to carry forward from the episodic plan, and if not, an appropriate item can be selected from the longitudinal plan content that matches the episodic goal or activity.

Ideally, goals and activities documented in a person's longitudinal plan are clearly measurable, so there is no ambiguity between the person and their care team around what is expected of them. To help facilitate this, the concept of a target is built into longitudinal plan goals and activities. Setting a target on a goal or activity allows users to outline the specific completion criteria required to meet or complete the goal or activity. This may be advantageous for a few reasons.

First, it allows the target expectations to be discretely and clearly documented to ensure that they do not have to be inferred from the description of the goal or activity. Second, it gives other systems (EMRs, patient portals, third-party content providers, etc.) the ability to understand the completion criteria of a given goal or activity, in case the other systems want to provide content or workflows that would facilitate the completion of that goal or activity. Lastly, it provides the framework to use targets in conjunction with other data in the longitudinal record to systematically understand if the person is meeting a target, which would therefore allow updates to the target to show its progress.

A target may be made up of two main components: 1) the concept that is being evaluated (called the "measure"); and 2) the details of how it should be evaluated. For example, one common goal for a diabetic would be to maintain the A1c level in an acceptable range. The target for that goal could be "A1c (the measure)<7% (how it is evaluated)". Targets can be built to evaluate numeric results via standard comparison operators (<, >, =, etc.) or by evaluating a range of results (A1c between 7%-9%). Targets can also be built to look for the existence of information. For example, a common wellness-focused activity for most people might be to get a flu shot every year. The target for that activity could be "Influenza immunization (the measure) exists in 2018 (how it is evaluated)."

One important thing to note about targets is that the measure defined for a target should map to a code roll-up in an ontology (a concept). Similar to how health concerns from the Longitudinal Plan are correlated to various EMRs using concepts, by using concepts in defining a target, flexibility in understanding what data could satisfy a target is provided. For example, a person's weight result could be codified a number of different ways across various systems. If a person had a weight-focused goal on their longitudinal plan, the weight measure may not be tied to a single, specific coding that has to be matched in order for a system to understand if its results satisfy the target. Instead, use of a concept supports weight results across a wide variety of codings, giving consuming systems more flexibility in understanding which results should satisfy a target. This is especially important when it comes to the longitudinal plan using data in a cloud-based, population health management system to understand if targets are satisfied, since data in the cloud-based, population health management system is aggregated from a variety of sources, each of which could have their own approach for how a given result type is codified. This means that a person in the cloud-based, population health management system can have multiple results for a single type of data (e.g., temperature) that is codified in different ways, simply because the various systems that captured those results for the person codified them differently.

With reference to FIGS. 5-16, illustrative screen displays 500-1600 of embodiments of the present invention are shown. It is understood that each of the illustrative screen displays are connected logically, such that they comprise a user interface designed for an intelligent touch care system, in accordance with embodiments of the present invention. The screen displays may appear in any order and with any number of screen displays, without regard to whether the screen display is described or depicted herein. The screen displays provide tools and features that provide integrated coordination of care, in accordance with embodiments of the present invention.

Figure 5:
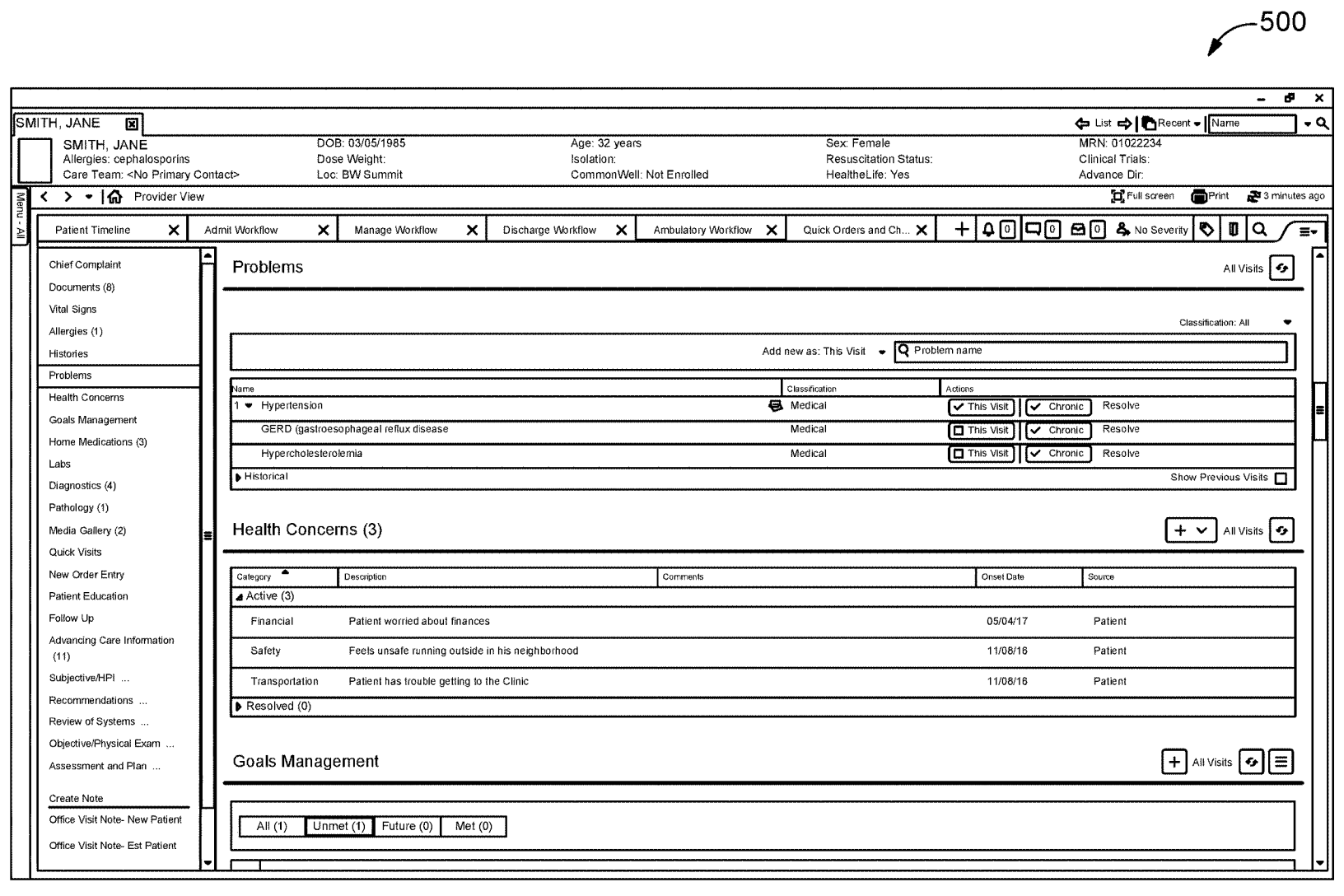
Figure 6:
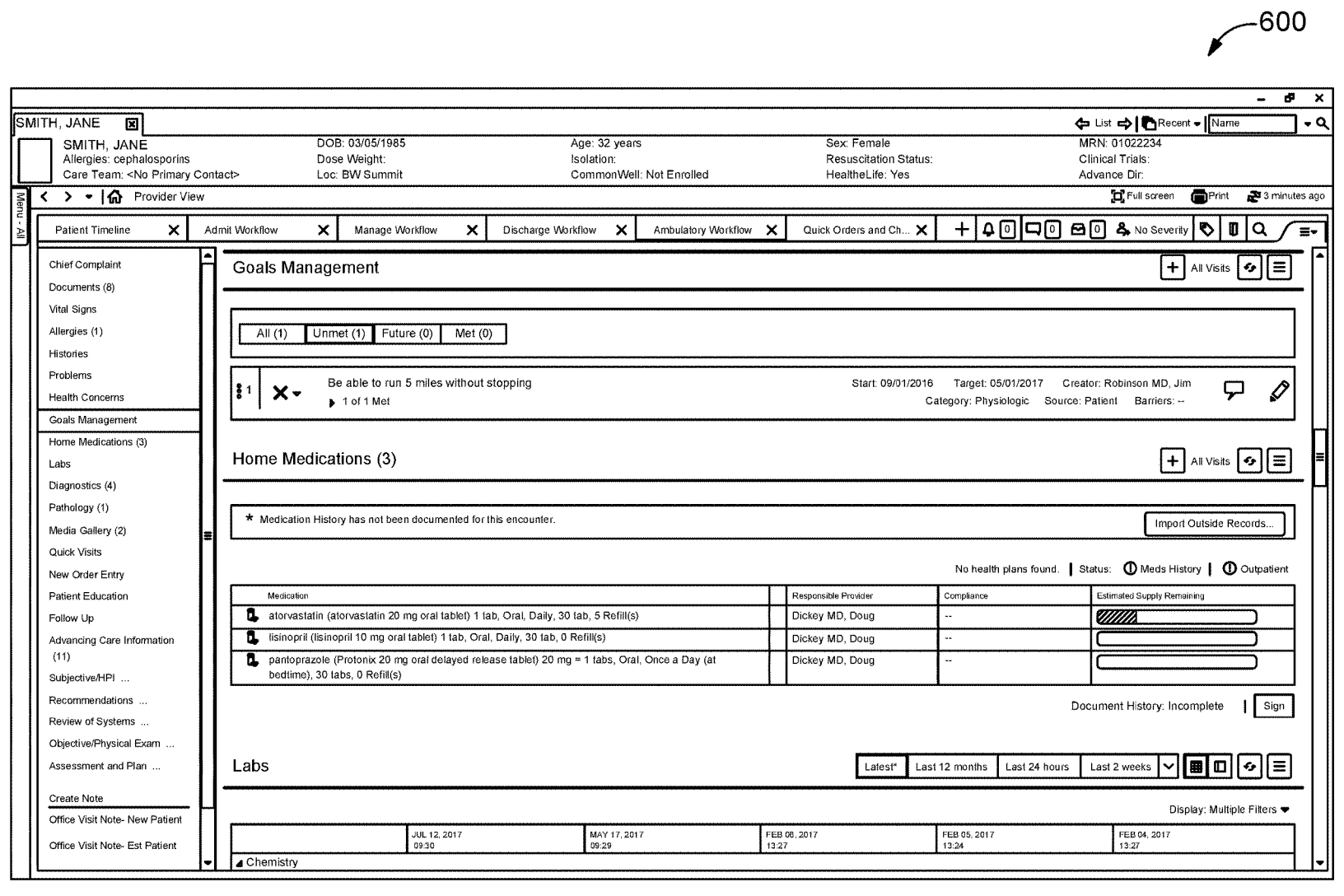
Figure 7:
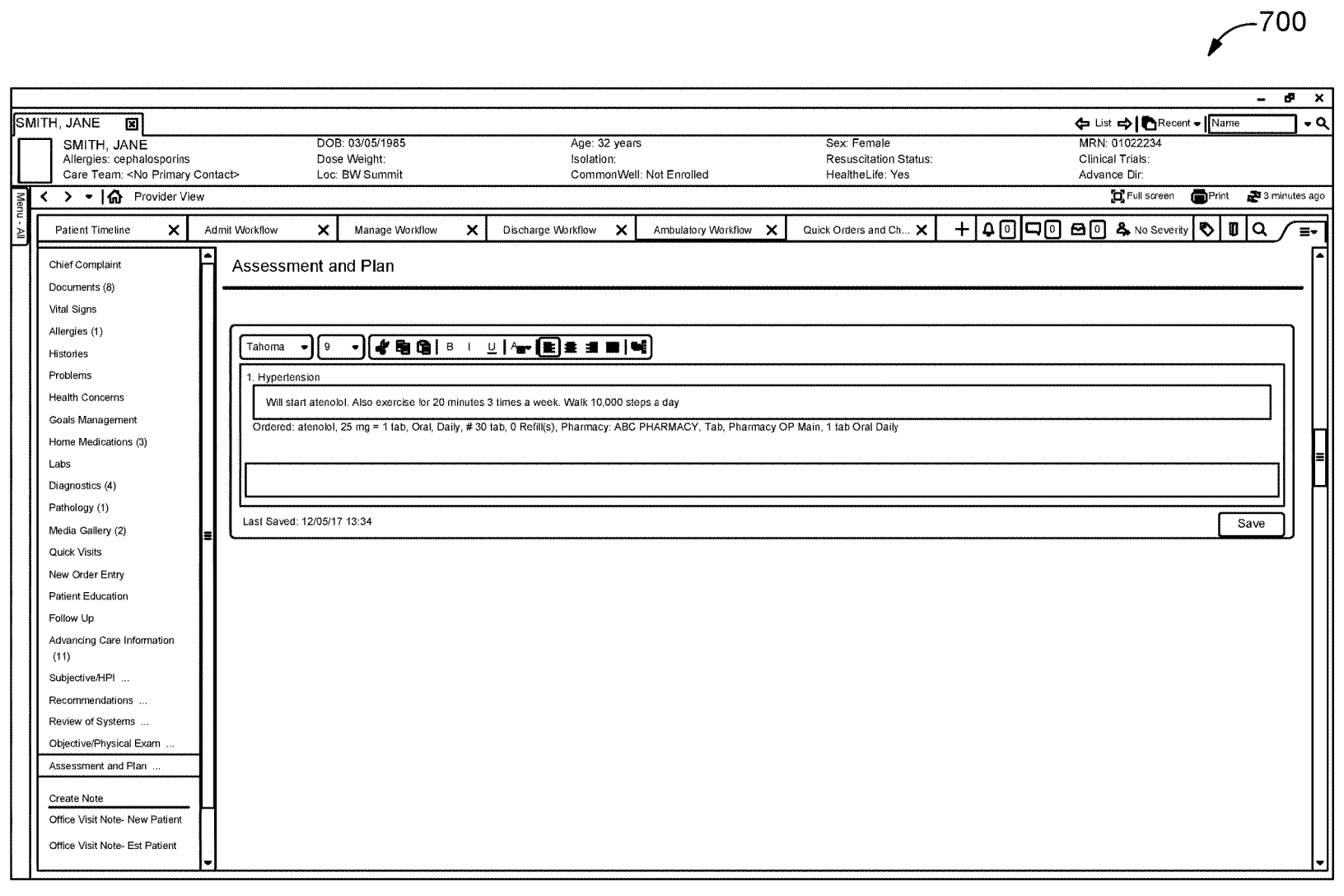

In FIGS. 5-7, screen displays 500-700 depict various items of data that can be utilized to recommend goals and activities for the patient. For example, in FIG. 5, problems and health concerns for the patient are collected by the one plan system and displayed. In FIG. 6, goals and medications for the patient are recommended/displayed. FIG. 7 illustrates an assessment and plan for the patient.

Figure 9:
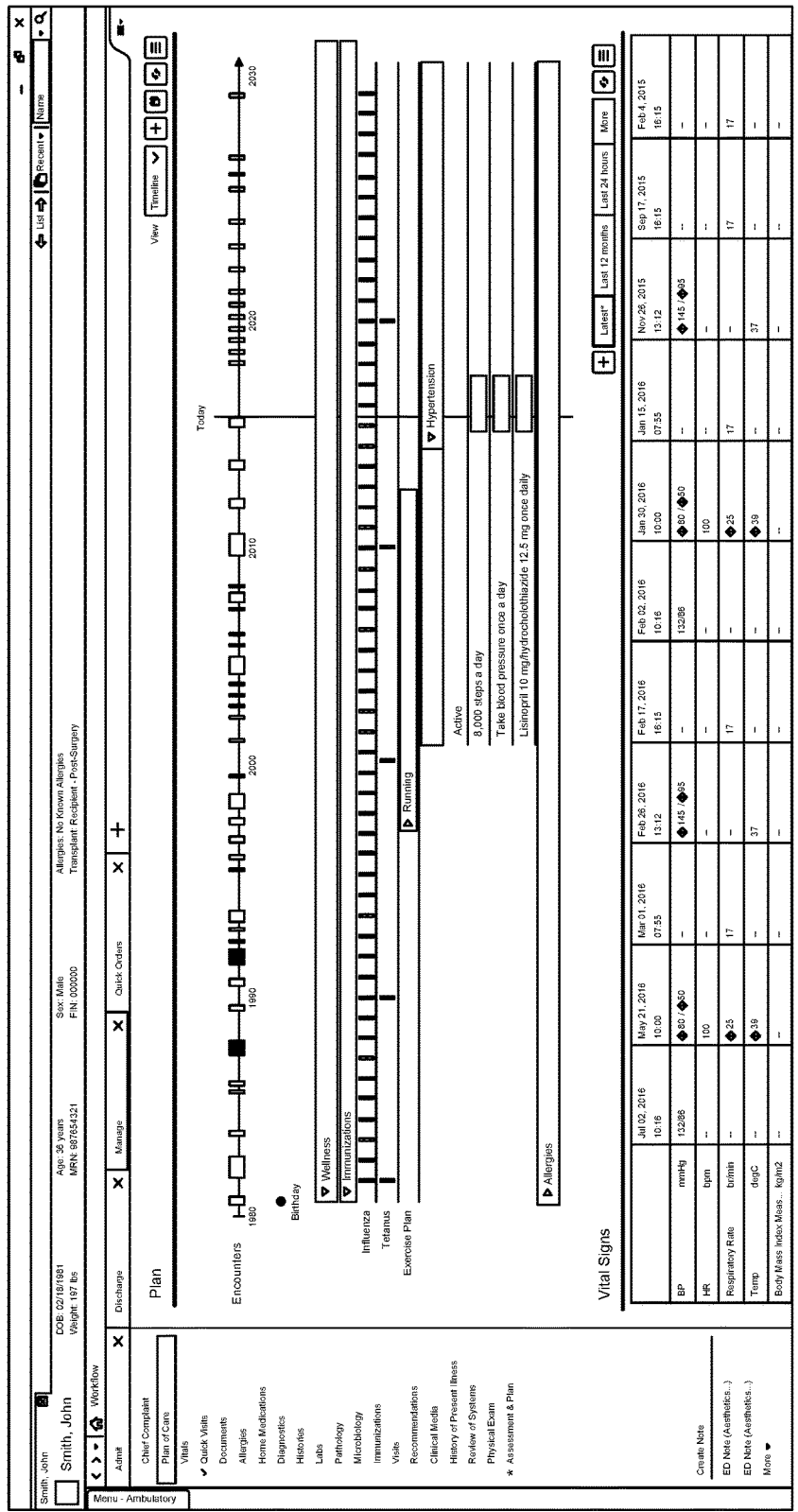
Figure 10:
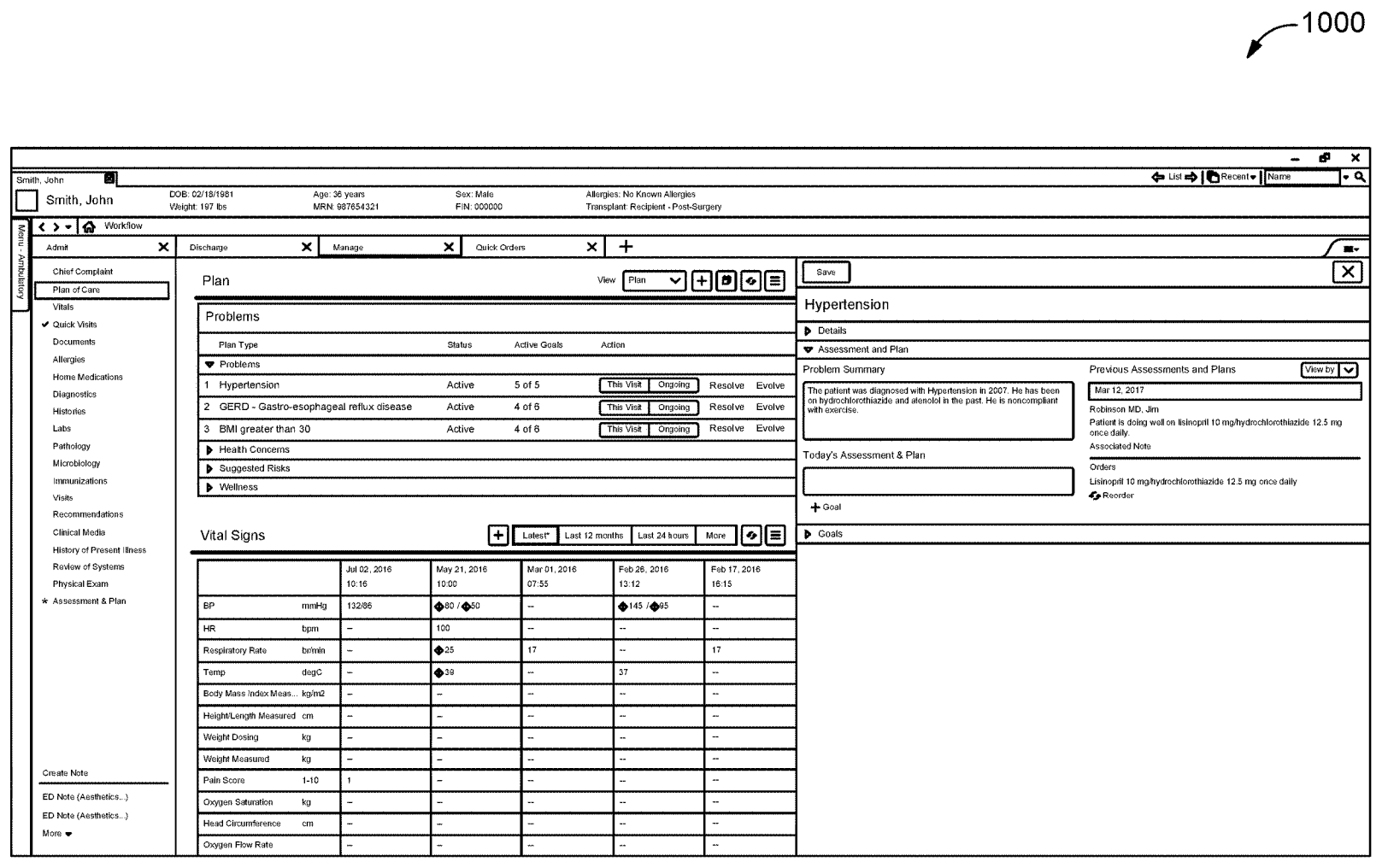
Figure 11:
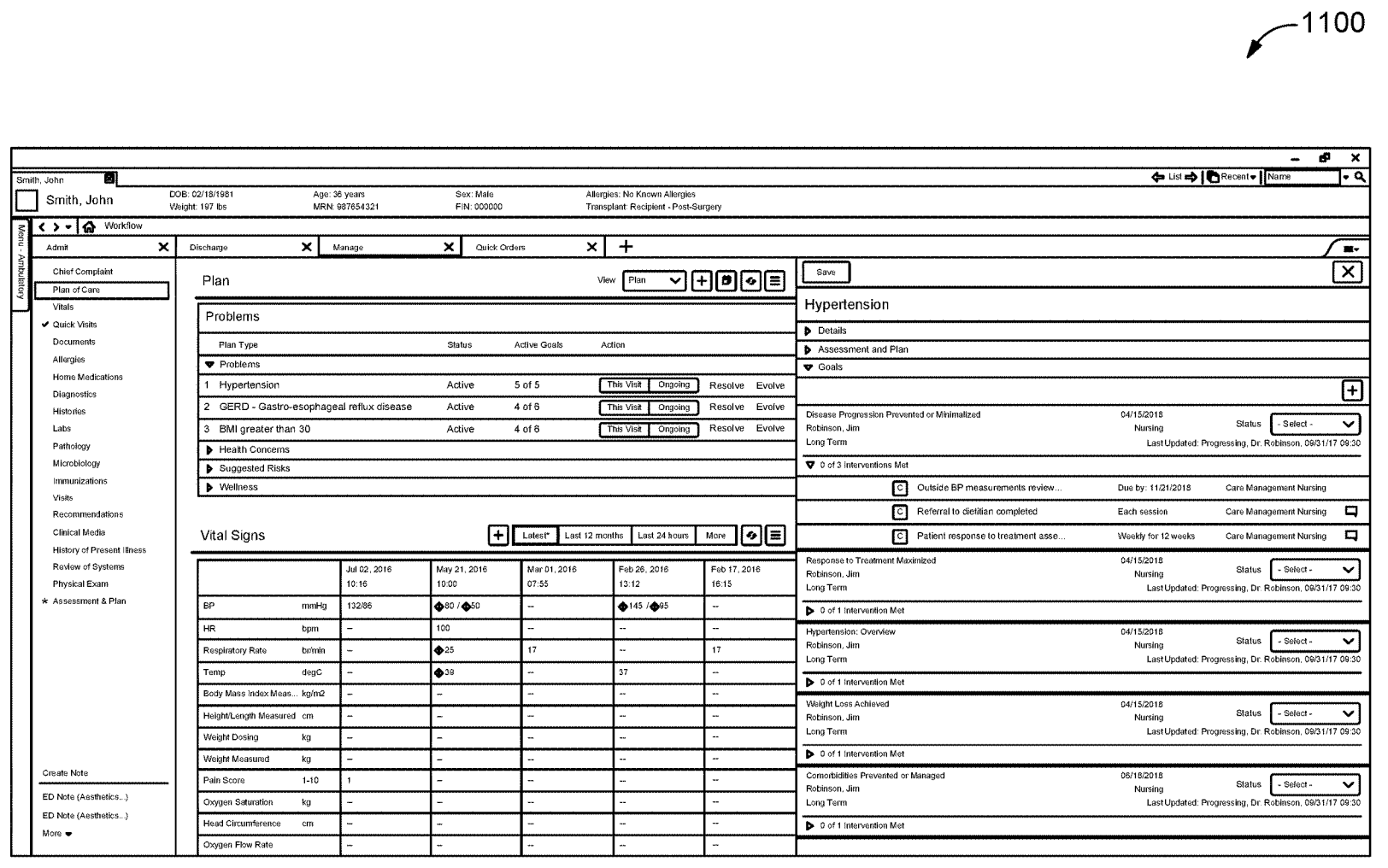
Figure 12:
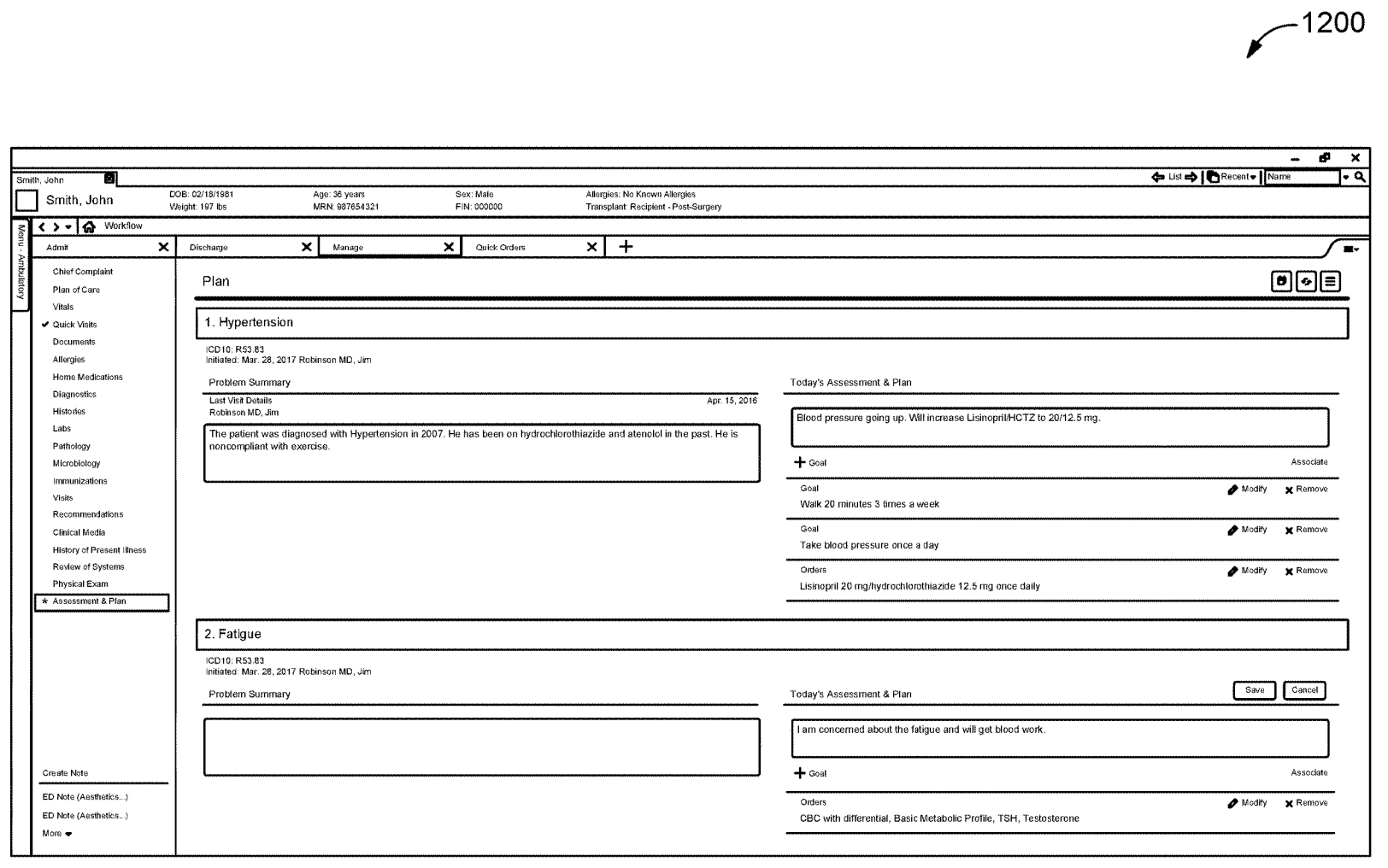

Turning to FIGS. 8-12, various aspects and details of the plan are illustrated. For example, in FIG. 8, the plan identifies several plan types for problems, as well as the status corresponding to the goals set for the patient with respect to each plan type. FIG. 9 illustrates a timeline corresponding to a plan. In FIGS. 10-11, details for a particular plan type are displayed. For example, FIG. 10 illustrates details corresponding to goals for a particular plan type. FIG. 11 illustrates details corresponding to an assessment and plan for the particular plan type. FIG. 12 illustrates the various plan elements integrated into clinician documentation.

Figure 13:
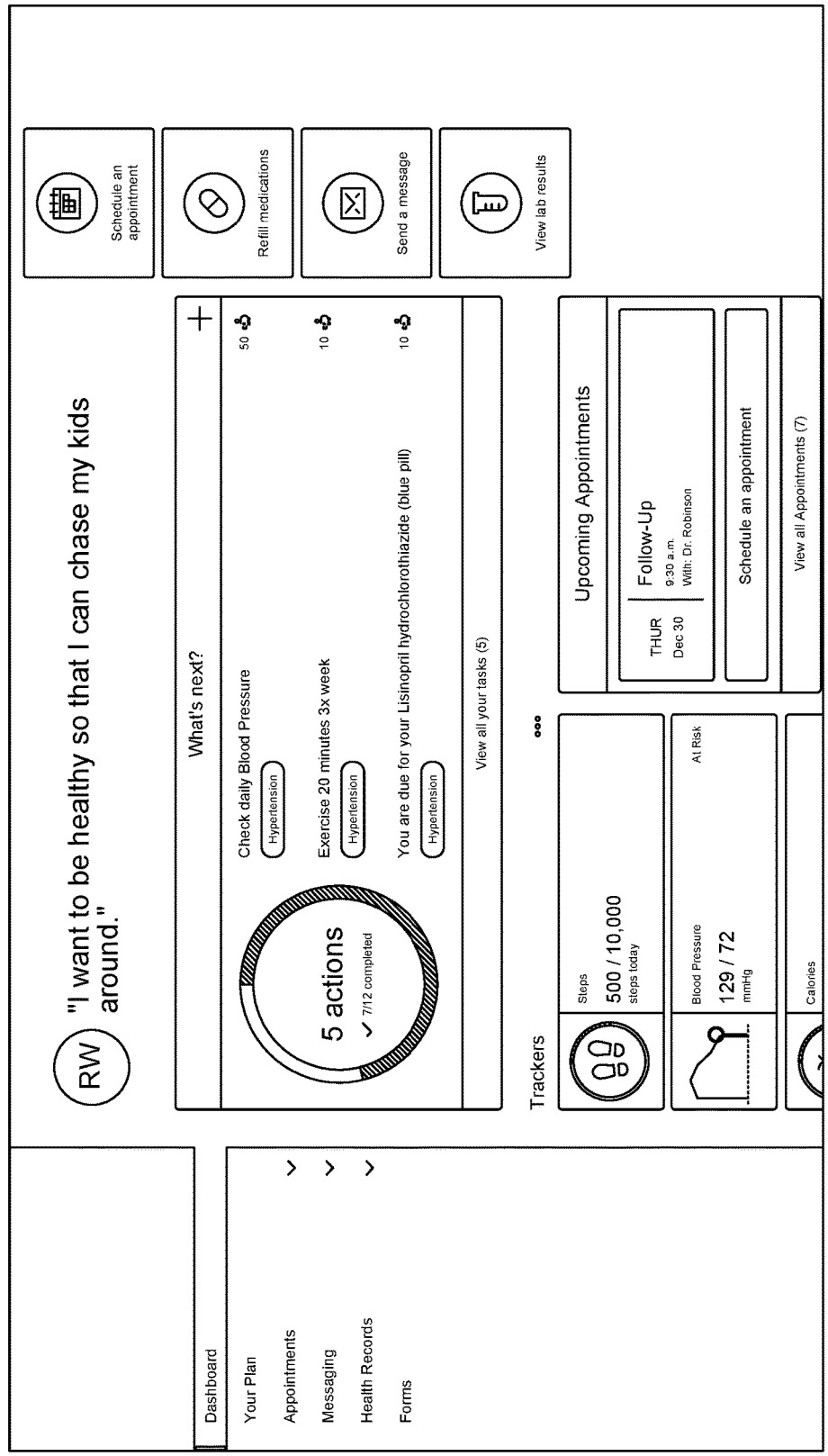
Figure 16:
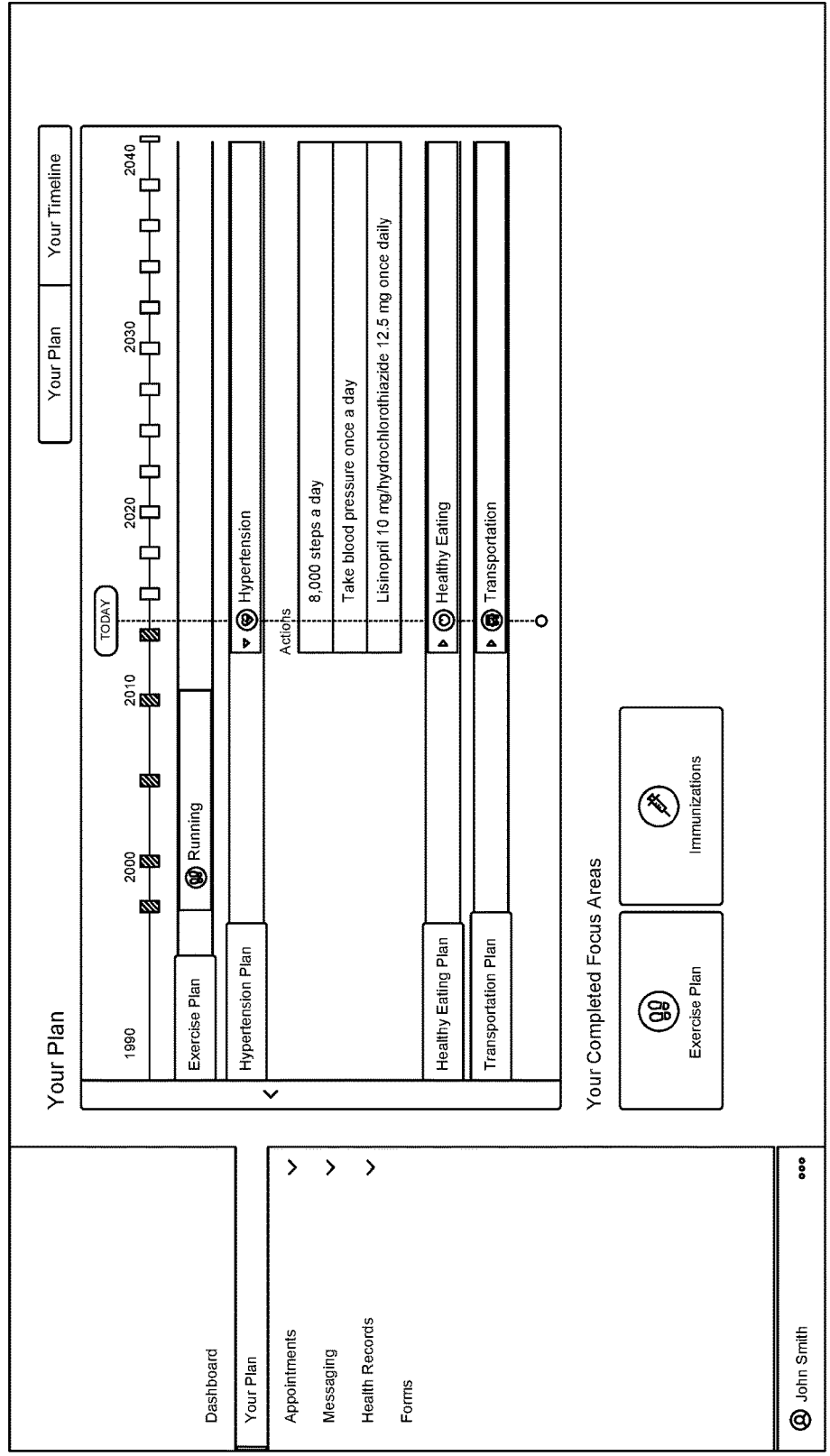

In FIGS. 13-16, various aspects and details of the plan are illustrated in a patient portal. FIGS. 13 and 14 depict various tasks to be performed by the patient, various trackers of goals for the patient, suggestions for the patient, and upcoming appointments. FIG. 15 illustrates similar tasks to be performed by the patient as those shown in FIG. 13, but with additional detail. In FIG. 16, a timeline representation of the plan is illustrated for the patient.

Figure 17:
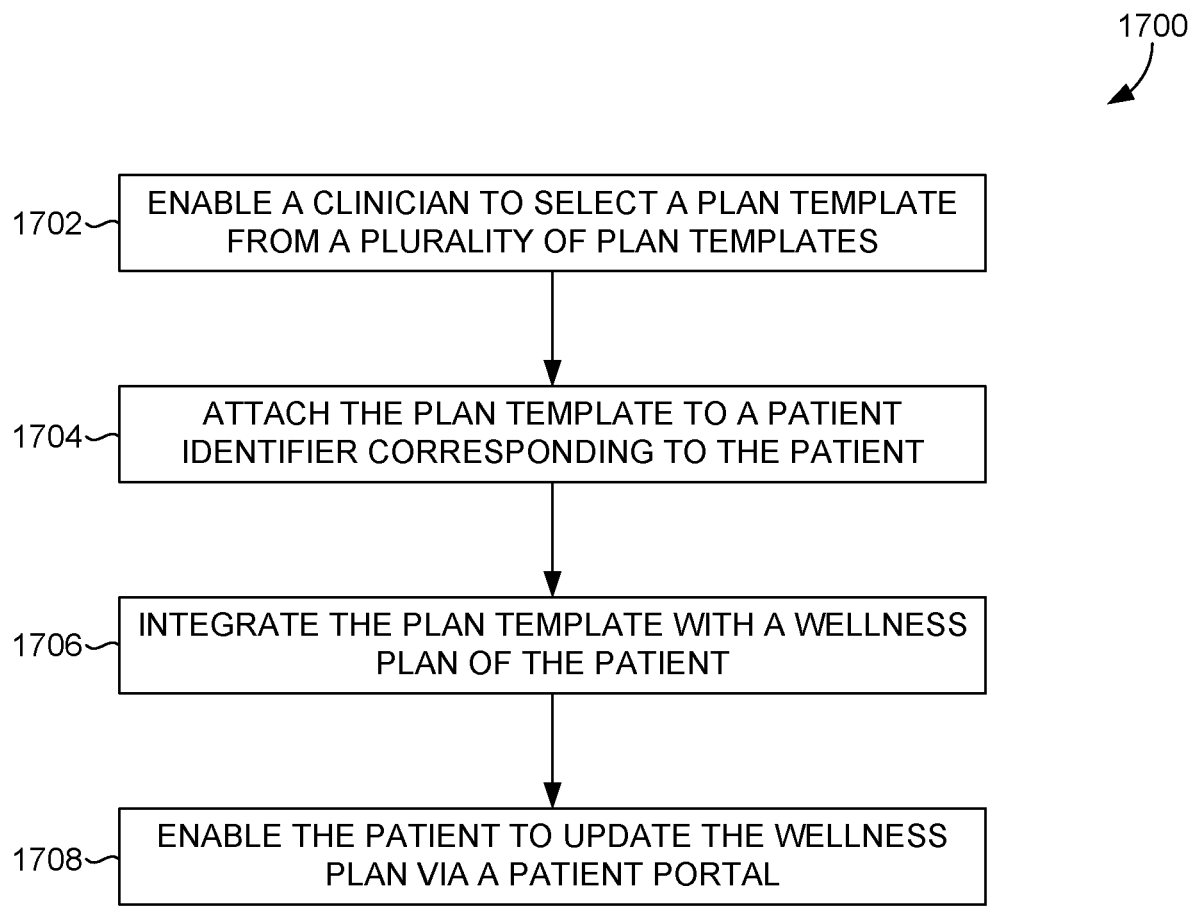
FIG. 17 depicts a flow diagram illustrating a method of providing an integrated coordination of care plan, in accordance with an embodiment of the present invention.

Referring now to FIG. 17, a flow diagram is provided illustrating a method 1700 for providing integrated coordination of care, in accordance with an embodiment of the present invention, in accordance with embodiments of the present invention. Method 1700 may be performed by any computing device (such as computing device described with respect to FIG. 1) with access to a one plan system (such as the one described with respect to FIGS. 2-4) or by one or more components of the one plan system.

Initially, at step 1710, a clinician is enabled to select a plan template from a plurality of plan templates. In embodiments, the plan template recommends goals, activities, and strengths that may be selected by the clinician. The plurality of plan templates may be searchable for a particular health concept. The plan template is attached, at step 1704, to a patient identifier corresponding to the patient. In embodiments, the patient identifier is attached to at least one electronic medical record of the patient. The plan template is integrated with a wellness plan of the patient, at step 1706. At step 1708, the patient is enabled to update the plan template via a portal.

In embodiments, the particular health concept corresponds to health concerns, social concerns, goals, and activities associated with the patient. A code corresponding to a problem documented in an electronic medical record (EMR) of the patient may be compared to a concept code for a health concern. Based on the comparing, the health concern may be created for the patient or information corresponding to the health concern may be retrieved from the EMR of the patient. Workflows for a clinician may additionally be embedded in an EMR of the patient.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory media having instructions that, when executed by one or more processors, cause a plurality of operations, the operations comprising:

enabling, at a longitudinal plan system, a user to select a plan template from a plurality of plan templates, the plurality of plan templates searchable for a particular health concept, wherein the particular health concept corresponds to health concerns, social concerns, goals, and activities associated with a patient;

attaching the plan template to a patient identifier corresponding to the patient;

determining that a code, corresponding to a problem documented in an electronic medical record (EMR) of the patient, is contained in a concept code for a health concern identified by the particular health concept;

responsive to determining that the code is contained in the concept code:

performing one or both of creating the health concern for the patient of and storing information corresponding to the health concern in the EMR of the patient; and embedding, in the EMR of the patient, a clinician workflow of a clinician, wherein the clinician workflow of the clinician is associated with the health concern;

creating a first electronic access, by provider care-team devices via a personnel application programmable interface (API), to enable modifying by the provider care-team devices of one or more information elements selected from a group comprising the EMR of the patient and the clinician workflow of the clinician; and creating a second electronic access, by a patient device via a patient API, to enable modifying by the patient device of one or several information elements selected from the group comprising the EMR of the patient and the clinician workflow of the clinician.

2. The one or more non-transitory media of claim 1, wherein the plan template recommends goals, activities, and strengths that may be selected by the clinician.

3. The one or more non-transitory media of claim 1, wherein the patient identifier is attached to at least one electronic medical record of the patient.

4. The one or more non-transitory media of claim 1, the operations further comprising presenting information associated with both the problem and the health concern in a single interface.

5. The one or more non-transitory media of claim 4, the operations further comprising receiving, via the interface, an update to the plan template for the patient.

6. The one or more non-transitory media of claim 5, the operations further comprising responsive to receiving the update to the plan template, updating the EMR of the patient.

7. The one or more non-transitory media of claim 1, wherein the concept code includes a code roll-up comprising a plurality of codes that represent the health concern, respectively, in a plurality of codings used by different systems.

8. A computerized method, comprising:
enabling, at a longitudinal plan system, a user to select a plan template from a plurality of plan templates, the plurality of plan templates searchable for a particular health concept, wherein the particular health concept corresponds to health concerns, social concerns, goals, and activities associated with a patient;
attaching the plan template to a patient identifier corresponding to the patient;
determining that a code, corresponding to a problem documented in an electronic medical record (EMR) of the patient, is contained in a concept code for a health concern identified by the particular health concept; and
responsive to determining that the code is contained in the concept code:
performing one or both of creating the health concern for the patient e and storing information corresponding to the health concern in the EMR of the patient; and
embedding, in the EMR of the patient, a clinician workflow of a clinician,
wherein the clinician workflow of the clinician is associated with the health concern;
creating a first electronic access, by provider care-team devices via a personnel application programmable interface (API), to enable modifying by the provider care-team devices of one or more information elements selected from a group comprising the EMR of the patient and the clinician workflow of the clinician; and
creating a second electronic access, by a patient device via a patient API, to enable modifying by the patient device of one or several information elements selected from the group comprising the EMR of the patient and the clinician workflow of the clinician.

9. The computerized method of claim 8, wherein the plan template recommends goals, activities, and strengths that may be selected by the clinician.

10. The computerized method of claim 8, wherein the patient identifier is attached to at least one electronic medical record of the patient.

11. The computerized method of claim 8, further comprising presenting information associated with both the problem and the health concern in a single interface.

12. The computerized method of claim 11, further comprising receiving, via the interface, an update to the plan template for the patient.

13. The computerized method of claim 12, further comprising responsive to receiving the update to the plan template, updating the EMR of the patient.

14. The computerized method of claim 8, wherein the concept code includes a code roll-up comprising a plurality of codes that represent the health concern, respectively, in a plurality of codings used by different systems.

15. A system having one or more processors configured to facilitate a plurality of operations, the operations comprising:
enabling, at a longitudinal plan system, a user to select a plan template from a plurality of plan templates, the plurality of plan templates searchable for a particular health concept, wherein the particular health concept corresponds to health concerns, social concerns, goals, and activities associated with a patient;
attaching the plan template to a patient identifier corresponding to the patient;
determining that a code, corresponding to a problem documented in an electronic medical record (EMR) of the patient, is contained in a concept code for a health concern identified by the particular health concept; and
responsive to determining that the code is contained in the concept code:
performing one or both of creating the health concern for the patient and storing information corresponding to the health concern in the EMR of the patient; and
embedding, in the EMR of the patient, a clinician workflow of a clinician,
wherein the clinician workflow of the clinician is associated with the health concern;
creating a first electronic access, by provider care-team devices via a personnel application programmable interface (API), to enable modifying by the provider care-team devices of one or more information elements selected from a group comprising the EMR of the patient and the clinician workflow of the clinician; and
creating a second electronic access, by a patient device via a patient API, to enable modifying by the patient device of one or several information elements selected from the group comprising the EMR of the patient and the clinician workflow of the clinician.

16. The system of claim 15, wherein the plan template is configured to recommend goals, activities, and strengths that may be selected by the clinician.

17. The system of claim 15, the operations further comprising presenting information associated with both the problem and the health concern in a single interface.

18. The system of claim 17, the operations further comprising receiving, via the interface, an update to the plan template for the patient.

19. The system of claim 18, the operations further comprising responsive to receiving the update to the plan template, updating the EMR of the patient.

20. The system of claim 15, wherein the concept code includes a code roll-up comprising a plurality of codes that represent the health concern, respectively, in a plurality of codings used by different systems.

* * * * *